United States Patent [19]

Medzius

[11] Patent Number: 5,040,411
[45] Date of Patent: Aug. 20, 1991

[54] WINDSHIELD MOISTURE SENSOR

[75] Inventor: Joseph Medzius, Mt. Lebanon, Pa.

[73] Assignee: PPG Industries, Inc., Pittsburgh, Pa.

[21] Appl. No.: 457,616

[22] Filed: Dec. 27, 1989

[51] Int. Cl.$^5$ .................. G01R 27/26; H01G 5/20
[52] U.S. Cl. ................................. 73/73; 361/286
[58] Field of Search ............. 73/73, 304 C; 361/286, 361/284

[56] References Cited

U.S. PATENT DOCUMENTS

| | | | |
|---|---|---|---|
| 3,523,244 | 8/1970 | Goodman et al. | |
| 3,986,110 | 10/1976 | Overall et al. | |
| 4,127,763 | 11/1978 | Roselli | 219/203 |
| 4,164,868 | 8/1979 | Suntola | 73/336 |
| 4,386,336 | 5/1983 | Kinomoto et al. | 338/35 |
| 4,429,343 | 1/1984 | Freud | 361/286 |
| 4,520,341 | 5/1985 | Miyoshi et al. | 338/35 |
| 4,522,060 | 6/1985 | Murata et al. | 73/336 |
| 4,639,831 | 1/1987 | Iyoda | 361/286 |
| 4,703,237 | 10/1987 | Hochstein | 318/483 |
| 4,705,998 | 10/1987 | Millerd et al. | 318/483 |
| 4,805,070 | 2/1989 | Koontz et al. | 361/286 |
| 4,831,493 | 5/1989 | Wilson et al. | 73/336.5 X |

Primary Examiner—Daniel M. Yasich
Attorney, Agent, or Firm—Andrew C. Siminerio

[57] ABSTRACT

A moisture sensor to sense rain on a windshield includes sensor members and leads on the outboard surface of the windshield. The members and leads are uncoated and directly exposed to any moisture accumulation on the sensor. Leads connect the sensor to a controller which includes a signal generator and sensor monitor. The relative spacing between the leads as compared to the spacing between the sensor members is such that the impedance of the sensor when the leads are electrically interconnected by moisture is measurably different from the sensor impedance when said members or said members and leads are electrically interconnected. In response to the latter signal, the windshield wipers are actuated.

29 Claims, 1 Drawing Sheet

WINDSHIELD MOISTURE SENSOR

BACKGROUND OF THE INVENTION

1. Field of the Invention

This invention relates to an apparatus for detecting moisture on a substrate, and in particular, to a moisture sensor positioned on a windshield that senses moisture to actuate a windshield wiper motor.

2. Technical Considerations

When operating a vehicle, it is important to maintain a clear, undistorted viewing area through the windshield of the vehicle. Windshield wiper mechanisms are provided to clear selected portions of the windshield of water and/or dirt that may obscure the vehicle operator's vision.

Moisture sensors have been used to sense rain on windshields and automatically actuate a windshield wiper motor to remove the water and clear the vision area. Some of these sensors include electrically conductive members having a protective coating on the exterior surface of the windshield. The conductive members are generally arranged in a fixed relationship to form variable capacitors whose output varies as a function of moisture absorbed by the overlaying protective coating. Other sensors use multiple pairs of conductive members and sequentially monitor the capacitance between the different pairs to determine the presence of moisture on the sensor.

PATENTS OF INTEREST

U.S. Pat. No. 3,523,244 to Goodman et al. teaches a sensor element for measuring absolute humidity substantially independently of the ambient temperature and pressure. An aluminum base member is coated with a thin, porous aluminum oxide layer. Electric connections are made to the oxide layer and base member. The capacitance and resistance between the two electrical connections varies in proportion to the absolute humidity or water vapor in the atmosphere to which it is exposed.

U.S. Pat. No. 3,986,110 to Overall et al. teaches a device for determining the depth of water accumulating on the surface of a pathway. The device includes a sensor having first and second capacitors positioned within a block of electrically insulating material in a spaced apart relationship.

U.S. Pat. No. 4,127,763 to Roselli teaches a heated rear window with a moisture sensor having high impedance. The sensor is placed on the inboard surface of the rear window adjacent to its printed heating grid. The sensor includes a pair of electrodes having interdigitated members. One electrode is connected to the heating grid while the other includes a conducting surface used to secure the electrode to a connection terminal.

U.S. Pat. No. 4,164,868 to Suntola teaches a capacitive humidity transducer having an electrically nonconductive base carrying at least a pair of spaced, electrically conductive coatings along the major surface of the base. A dielectric film which is active with respect to water absorption is also carried by the base and covers at least a portion of the coatings. The dielectric film has a dielectric constant which varies as a function of the extent to which water has been absorbed by the film. An outer, electrically conductive, water-permeable layer is supported by the dielectric film. The dielectric film maintains the outer layer permanently out of contact with at least one of the coatings so that it is possible to measure a capacitance between these coatings, which is indicative of humidity in the atmosphere.

U.S. Pat. No. 4,386,336 to Kinomoto et al. teaches a humidity sensor with spaced apart electrode members that are covered with a high molecular weight humidity sensitive material containing a reactive cationic monomer unit.

U.S. Pat. No. 4,429,343 to Freud teaches a humidity-sensing element having two sets of interdigitated, thin film platinum fingers deposited on the surface of a glass substrate. The film is covered by a coating of water-absorbing material such as cellulose acetate butyrate or silicone rubber. The humidity sensitivity of the sensor results from the humidity-related dielectric constant change which occurs in the coating over the fingers. As this dielectric constant changes, so does the capacitance between the interdigitated fingers.

U.S. Pat. No. 4,520,341 to Miyoshi et al. teaches a moisture sensor having a moisture responsive organic membrane and protective layer covering a pair of electrically conductive members. The organic membrane consists essentially of a crosslinked organic polymer having a hydrophilic group.

U.S. Pat. No. 4,522,060 to Murata et al. teaches a dry/dew/frost sensor comprised of a plurality of sensor units. Each sensor unit includes a ceramic substrate whose permittivity is lower than ice and a pair of electrodes being arranged on the ceramic substrate in contact therewith, wherein adjacent sensor units are arranged so as to face each other at a predetermined distance so that the pair of electrodes may be opposed to each other, and the impedance between the pair of electrodes on each of the sensor unit varying with changes in three states: dry, dewed, and frosted.

U.S. Pat. No. 4,639,831 to Iyoda teaches a transparent sensor for detecting rain on window glass located within the wiping area on the exterior surface of the window glass. The sensor includes a pair of spaced apart electrodes having interdigitated finger members that are insulated electrically from each other by a transparent insulating protective film. The interdigitated members form capacitors having variable capacitance. When a drop of water accumulates on a portion of the protective coating between a pair of finger members, the capacitance of the capacitor becomes greater than the normal capacitance because the dielectric constant of the drop of water on the protective coating is greater than the dielectric constant of air. Accordingly, as the number of drops of water on the protective coating increases, the total capacitor output increases.

U.S. Pat. No. 4,703,237 to Hochstein teaches a rain sensor having a passive circuit supported on a window which has an initial resonant frequency. A generating means creates an electromagnetic field having a range of frequencies wherein the initial resonant frequency is within the range of frequencies. When moisture collects about the passive circuits, the resonant frequency of the passive circuit shifts away from the initial resonant frequency which can be sensed by a detector.

U.S. Pat. No. 4,705,998 to Millerd et al. teaches an automatic window wiper control having a plurality of individual sensing circuits connected to a multiplexer arrangement that sequentially energizes and de-energizes the circuits. Any voltage build-up between adjacent monitored circuits due to moisture is stored in a capacitor that continually bleeds to a ground. When the capacitor is overcharged, circuitry is activated.

U.S. Pat. Nos. 4,805,070 to Koontz et al. and 4,831,493 to Wilson et al. teach a windshield moisture sensor with exposed sensor members. Leads to the members are electrically insulated from each other to prevent shorting of the sensor when water accumulates between the leads. In Koontz et al., the leads to the sensor are positioned within the windshield on the inboard surface of its outer glass ply. In Wilson et al., at least one of the leads to the sensor is either positioned within the windshield or coated with a protective coating.

SUMMARY OF THE INVENTION

The present invention provides a sensor to detect moisture on a vehicle windshield. First and second closely spaced, exposed electroconductive members, such as a metallic film or cured ceramic paint, are secured to the outboard surface of a windshield. The sensor members are preferably abuse resistant because they are uncovered and directly exposed to the environment and the wiping action of the windshield wipers. The members include interdigitated fingers to increase the length of the interface therebetween. The sensor is interconnected to an electrical signal generator and a controller that monitors a selected characteristic of the sensor. The spacing of the uncoated leads relative to the spacing of the uncoated interdigitated fingers of the sensor is such that the monitored characteristic of the sensor when the entire sensor is dry or when only the leads are electrically interconnected, for example by moisture or salt deposits on the windshield, is measurably different from the monitored characteristic when moisture accumulates on the windshield sensor and bridges the space between the interdigitated fingers of the first and second exposed electroconductive members. When the monitored characteristic of the sensor is indicative of this latter condition, the controller generates a signal to energize the windshield wiper motor which clears the outboard surface of the windshield.

In one particular embodiment of the invention, the monitored characteristic of the sensor is its impedance. The spacing between the leads relative the spacing between the fingers is such that the magnitude of the sensor's impedance is significantly higher when the sensor is dry or only the leads are wet as compared to its impedance when the entire sensor is covered with moisture.

DETAILED DESCRIPTION OF THE INVENTION

The present invention is discussed with its use in conjunction with a laminated windshield construction, but it should be appreciated that the invention may be used in any application where it is desired to sense surface moisture.

Figure 1:
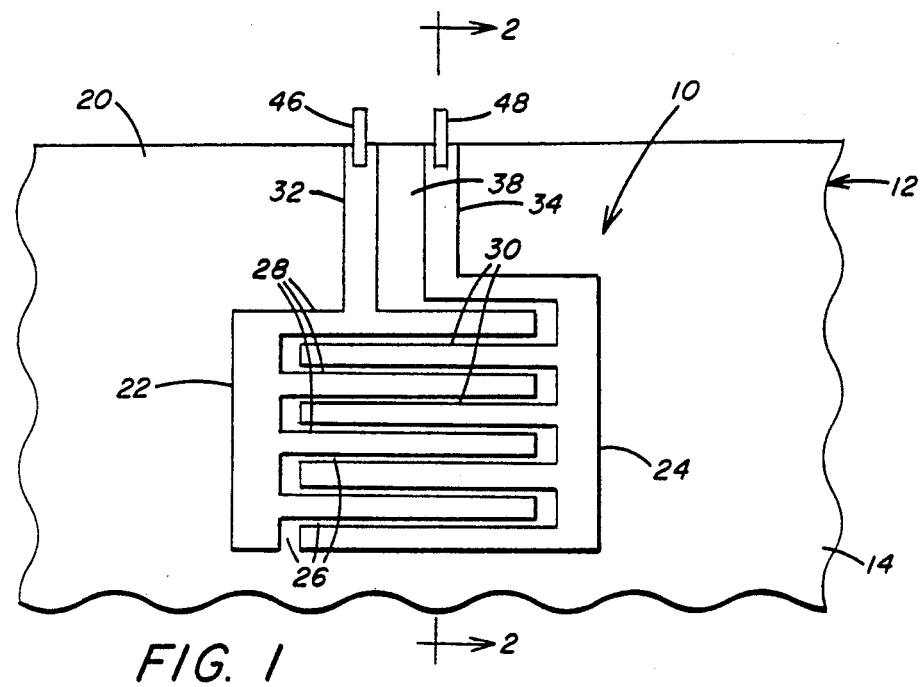
FIG. 1 is a plan view of a moisture sensor incorporating features of the present invention.
Figure 2:
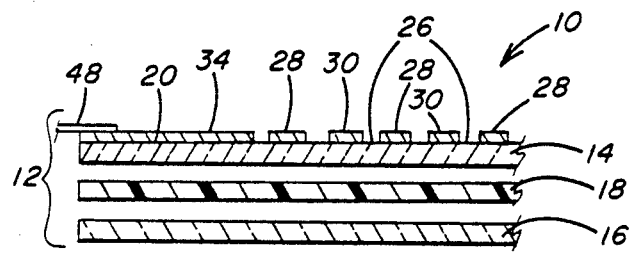
FIG. 2 is an exploded view through line 2—2 of FIG. 1 illustrating interdigitated conductive members of the uncoated electroconductive coating members and electrical lead connectors of the present invention.

Referring the FIGS. 1 and 2, a moisture sensor 10, which is the subject of the present invention, is incorporated in a conventional trilayer windshield 12 which includes an outer glass ply 14, inner glass ply 16 and flexible interlayer 18. The sensor 10 may be positioned anywhere on the windshield 12, but preferably is located in an area that is swept by the windshield wipers (not shown) as they clear the viewing area of the windshield 12.

In the particular embodiment of the invention illustrated in FIGS. 1 and 2, the outer surface 20 of the outer ply 14 includes two electroconductive members 22 and 24 spaced apart and electrically insulated from each other by gap 26 of predetermined width. Although not limiting in the present invention, the gap 26 is preferably not greater than the width of a rain drop or mist droplet that may impact or accumulate on the windshield 12. Unlike other moisture sensors, there is not protective coating over the members 22 and 24 so that they are exposed. As a result, the members 22 and 24 should be abuse resistant, i.e. abrasion, solvent, and weather resistant.

The members 22 and 24 may be positioned along the outer surface 20 of ply 14 by any technique that will not adversely affect the optical quality of the windshield 12 and may be any of a number of different types of electroconductive coatings or materials, as disclosed in U.S. Pat. No. 4,831,493 to Wilson et al., which teachings are incorporated by reference. Although not limiting in the present invention, the members 22 and 24 are preferably an electroconductive film, such as a tin oxide coating, deposited on the surface 20 of ply 14 by vacuum or pyrolytic deposition techniques. The members 22 and 24 may be interdigitated with projections 28 of member 22 positioned between and spaced from complementing projection 30 of member 24. The interdigitation increases the length of the interface between members 22 and 24, as will be discussed later. Gap 26 electrically insulates projections 28 from projections 30.

It should be noted that the thinner the coatings 22 and 24, the better a windshield wiper (not shown) can remove water accumulated in the gap 26 as the wiper sweeps across sensor 10, as will be discussed later.

Figure 3:
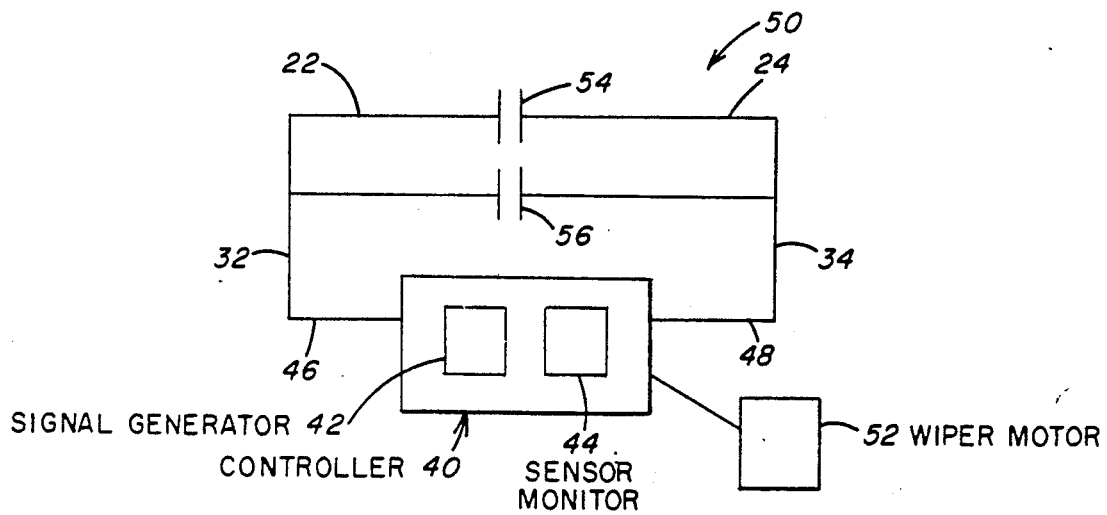
FIG. 3 is a schematic of a circuit that may be used in the practice of the invention.

With continued reference to FIGS. 1 and 2, the sensor 10 also includes lead members 32 and 34 which extend from members 22 and 24, respectively, along surface 20 of outer ply 14 and terminate at edge 36 of the windshield 12. Although not limiting in the present invention, in the particular embodiment illustrated in FIGS. 1 and 2, the leads 32 and 34 are adjacent to each other, separated by a gap 38 (shown only in FIG. 1) of predetermined width. The lead members 32 and 34 are electrically connected to a controller 40 as shown in FIG. 3, which monitors the sensor 10 as will be discussed later. Although not limiting in the present invention, controller 40 includes an AC signal generator 42 and sensor monitor 44 and is connected to leads 32 and 34 by wires 46 and 48, respectively. As with members 22 and 24, lead members 32 and 34 are uncoated so they should be abrasion, solvent, and weather resistant. Lead members 32 and 34 may be applied in any convenient manner known in the art and are preferable a tin oxide coating applied to surface 20 at the same time and in the same manner as members 22 and 24 are applied.

The sensor 10 has specific characteristics based on its particular configuration, such as for example its impedance. These characteristics may change when moisture is on the sensor 10. As a result, the presence of moisture on the sensor 10 can be determined by monitoring such a characteristic of the sensor 10. However, during operation of the moisture sensor 10 as described in this disclosure, it has been observed that moisture or other deposits which form an electrically conductive surface, e.g. salt or the vehicle body (not shown) that surrounds the windshield 12, may electrically interconnect the leads 32 and 34, shorting a portion of sensor circuitry 50 (shown schematically in FIG. 3) formed by members 22 and 24 and leads 32 and 34 so as to activate the windshield wiper motor when it is not required to operate. To avoid this condition, the present invention provides for a spacing between the leads 32 and 34 relative to the spacing between adjacent projections 28 and 30 of members 22 and 24, respectively, such that a monitored characteristic of the sensor 10 will indicate the overall moisture condition of the sensor 10. To put it another way, based on the relative width of gap 38 between leads 32 and 34 as compared to the width of gap 26 between projections 28 and 30, the characteristic of the sensor 10 monitored by the controller 40 varies depending on the following operating conditions: (1) when sensor 10 is dry; (2) when water electrically interconnects leads 32 and 34 only; (3) when water electrically interconnects the projections 28 and 30 only; (4) when both the projections 28 and 30 and leads 32 and 34 are electrically interconnected by water on the sensor 10.

Although not limited in the present invention in one particular embodiment, the monitored characteristic of the sensor 10 is its impedance. Impedance is expressed in terms of its magnitude in ohms and the phase shift in degrees between the current and voltage waves of the sensor 10 when driven by generator 42 as the sensor 10 changes from being highly resistive in nature, i.e. having a low phase angle, to highly capacitive, i.e. having a high phase angle. In the present invention, the relative spacing between the leads 32 and 34 and projections 28 and 30 is such that the impedance of the sensor 10 under operating conditions (1) and (2) is significantly different from its impedance under operating conditions (3) and (4). Based on the monitored impedance of the sensor 10, controller 40 can either activate a wiper motor 78 (shown in FIG. 3 only) when the monitored impedance is indicative of moisture bridging members 22 and 24, i.e. operating conditions (3) or (4), or either not actuate or inactivate the wiper motor 52 when the monitored impedance is indicative of operating conditions (1) or (2).

the sensor 10 and the voltage across the sensor 10. As an alternative, either the current or voltage may be fixed so that only the other has to be monitored by the monitor 44. Variations in the impedance of the sensor 10 as measured by monitor 44, are monitored by controller 40 which includes a bandpass circuit or a filter that will activate the wiper motor 52 only when the sensor impedance has a predetermined relationship relative to a predetermined reference value or in the alternative, is within a predetermined range, indicative of the condition when moisture has accumulated on the sensor 10. In particular, when there is no moisture accumulation between member projections 28 and 30 of the sensor 10, the sensor 10 will have an impedance indicative of the operating conditions (1) or (2) and controller 40 will not activate or deactivate the wiper motor 52. However, when water accumulates between projections 28 and 30 of the sensor 10, the sensor 10 will have an impedance indicative of operating conditions (3) or (4). Under the latter condition, controller 40 will generate a signal which will activate the wiper motor 52.

Testing was performed to examine the variations in the impedance of the sensor 10 under different operating conditions and signal inputs. In the particular embodiment of the sensor 10 used during testing, the coating members 22 and 24, including projections 28 and 30, respectively, and leads 32 and 34 were a transparent, tin oxide film applied by to a glass surface by pyrolytic deposition techniques, as taught in U.S. Pat. No. 3,677,814 to Gillery, which teachings are hereby incorporated by reference, providing a surface resistivity preferably in the range of 100 to 700 ohms per square. The leads 32 and 34 were approximately 9/32 inches (7.1 mm) wide with the gap 38 between the leads being approximately ⅝ to ¾ inches (16 to 19 mm). Each projection 28 and 30 was approximately 3/16 inches (0.48 cm) wide with the gap 26 between the projections being approximately 1/16 to 5/32 inches (1.6 to 4.0 mm). The testing was performed using a Hewlett Packard Model 4194A Impedance/Gain-Phase Analyzer. Table 1 presents the test results at selected input signal frequencies and are indicative of the overall test results. Each impedance value in Table 1, expressed in terms of its magnitude and phase angle, represents the impedance for the particular sensor configuration at a particular frequency and under the particular operating condition.

TABLE 1

| Operating Condition | Impedance of Sensor 10 Signal Input Frequency | | | |
| --- | --- | --- | --- | --- |
|  | 255 HZ | 505 HZ | 1,000 HZ | 1,978 HZ |
| Condition (1) No Moisture on Sensor | 5.8MΩ @ 86° | 3MΩ @ 86° | 1.6MΩ @ 86° | 0.81MΩ @ 86° |
| Condition (2) Moisture on Leads Only | 119KΩ @ 1.8° | 119KΩ @ 2.6° | 118KΩ @ 4.3° | 117KΩ @ 7.9° |
| Condition (3) Moisture on Projections Only | 24KΩ @ 0.32° | 24KΩ @ 0.39° | 24KΩ @ 0.33° | 24KΩ @ 0.45° |
| Condition (4) Moisture on Leads and Projection | 21KΩ @ 0.52° | 21KΩ @ 0.41° | 21KΩ @ 0.47° | 21KΩ @ 0.71° |

FIG. 3 is a schematic of a circuit 50 of the sensor 10 with the interdigitated projections 28 and 30 and leads 32 and 34 being represented by capacitors 54 and 56, respectively. Signal generator 42 powers the sensor 10 through leads 32 and 34. Although not limiting in the present invention, in the particular embodiment where the impedance of the sensor 10 is being monitored, the monitor 44 includes circuitry to monitor the current in Referring to Table 1, it can be seen that the magnitude of the impedance of sensor 10 under operating conditions (1) and (2) at the selected input frequencies is almost five times the impedance of the sensor 10 under operating conditions (3) and (4). In addition, the reduction in phase angle difference from nearly 90° to nearly 0° indicates that as moisture coats the sensor 10, the sensor 10 changes from being highly capacitive to highly resistive in nature.

In the previous discussion, the monitored characteristic of the sensor 10 used to activate the wiper motor 52 was the sensor impedance. However, other characteristics of the sensor 10 which change when moisture is on the sensor 10 may be used to monitor the sensor operation conditions. Although not limiting in the present invention, the reactance of the sensor 10 can be monitored and used to activate wiper motor 52. The reactance is the reactive component of impedance, which when added vectorially to the resistive component, forms the total impedance. Table 2 illustrates the reactance of the sensor 10 based on the impedance values shown in Table 1.

TABLE 2

| | Reactance of Sensor 10 | | | |
| --- | --- | --- | --- | --- |
| | Signal Input Frequency | | | |
| Operating Conditions | 255 HZ | 505 HZ | 1,000 HZ | 1,978 HZ |
| Condition (1) No Moisture on Sensor | 3.8MΩ | 4.0MΩ | 1.6MΩ | 0.81MΩ |
| Condition (2) Moisture on Leads Only | 3.7KΩ | 5.4KΩ | 8.9KΩ | 16.1KΩ |
| Condition (3) Moisture on Projections Only | 0.13KΩ | 0.16KΩ | 0.14KΩ | 0.19KΩ |
| Condition (4) Moisture on Leads and Projections | 0.19KΩ | 0.15KΩ | 0.17KΩ | 0.26KΩ |

As can be seen from Table 2, the reactance of the sensor 10 under operating conditions (3) and (4) is in the range of about 20 to 85 times less than the reactance of the sensor under operating condition (2) and is several orders of magnitude less than the reactance under operating condition (1). Because of the large difference between the sensor reactance under activating and nonactivating conditions, controller 40 can be precisely adjusted to activate the motor 52 only under the proper operating conditions.

In the previous discussion, it was shown that the impedance and reactance of the sensor 10 are significantly different under operating conditions (1) and (2) as compared to operating conditions (3) and (4). However, it should be appreciated that the magnitude of the measurable difference depends on several factors including, but not limited to, the frequency of the power source, the monitored characteristic of the sensor, e.g. impedance or reactance, the sensitivity of the monitoring control circuit, and the sensor configuration, and in particular the relative spacing between projections 28 and 30 as compared to the spacing between leads 32 and 34. In practice, once the sensor configuration is set and the power source is established, the control circuitry of the controller 40 is designed to activate the wiper motor 52 only when the monitored characteristics of the sensor is within or exceeds a predetermined activation range which, in turn is based on the overall sensor design. Although the characteristic of the sensor 10 monitored during testing, i.e. the impedance and reactance, changed on the order of 5 times to several orders of magnitude depending on the operating conditions as shown in Tables 1 and 2, it is obvious that depending on the sensitivity of the sensor controller 40, much smaller variations in the measured characteristic can be used to activate the wiper motor 52. It is believed that measurable differences as little as 1 to 2% or less can be used to activate the wiper motor 52.

When activated, the wiper motor 52 may operate to put the wipers in one of several modes. If desired, the windshield wipers (not shown) may make a single pass across the windshield 12 to clear any accumulated water from the sensor 10 or operate for a given time period or set number of passes. In addition, the control circuitry of windshield wipers (not shown) may be such that if the motor 52 is repeatedly activated so as to move the wipers to make a predetermined number of passes within a set time period, the motor 52 will remain activated until it is manually switched off by the vehicle operator.

The sensor 10 shown in FIGS. 1 and 2 may be used in a windshield having a bilayer construction (not shown), i.e. a windshield having a single outer glass ply and an inner impact-absorbing antilacerative ply, with the members 22 and 24 and leads 32 and 34 of the sensor 10 positioned along the outer surface of the glass ply in a manner as discussed previously. In addition, the sensor 10 may be used in combination with an electrically heated windshield as disclosed in U.S. Pat. No. 4,820,902 to Gillery, which teachings are incorporated by reference. Furthermore, the sensor 10 is not limited to use only on the outboard surface of a windshield. For example, the sensor 10 may be used to detect fog or ice on the inboard surface of vehicle window by locating members 22 and 24 on the inboard surface of the glass ply.

Unlike other rain sensors which constantly monitor variations in capacitance caused by moisture absorbent coatings or dielectric substrates, there are no variations in sensor 10 due to changes in moisture absorption because there is no coating over coating members 22 and 24 or leads 32 and 34 and there is no water absorbent dielectric positioned between the members or lead. The sensors of the present invention requires only that the spacing between the leads 32 and 34 relative to the spacing between the projections 28 and 30 of members 22 and 24 be such that a monitored characteristic of the sensor is measurably different under the different operating conditions.

The forms of this invention shown and described in this disclosure represent illustrative embodiments and it is understood that various changes may be made without departing from the scope of the invention as defined in the following claims.

I claim:
1. A sensor for detecting moisture comprising:
a dielectric substrate:
first and second electroconductive members positioned adjacent to each other and secured along a first major surface of said substrate and spaced apart a first predetermined distance, wherein adjacent portions of said first and second members have exposed, uncoated electroconductive surfaces;
first and second electroconductive leads extending from said first and second electroconductive members, respectively, and secured along said substrate surface wherein said leads are spaced apart a second predetermined distance and portions of said leads have exposed, uncoated electroconductive surfaces;
means to permit electrical connection of said leads to a signal generator; and
means to permit electrical connection of said leads to a monitoring means capable of detecting variations in a predetermined characteristic of said sensor, wherein said first predetermined distance is sufficiently different from said second predetermined distance so that said monitored characteristic of said sensor when said leads are electrically interconnected by moisture therebetween is measurably different from said monitored characteristic when said electroconductive members or said electroconductive members and leads are electrically interconnected by moisture therebetween.

2. The sensor as in claim 1 wherein said predetermined characteristic is the impedance of said sensor and wherein said first predetermined distance is sufficiently different from said second predetermined distance so that said monitored sensor impedance when only said electroconductive leads are electrically interconnected by moisture therebetween is measurably different from said monitored sensor impedance when said electroconductive members or said electroconductive members and leads are electrically interconnected by moisture therebetween.

3. The sensor as in claim 1 wherein said substrate and said electroconductive members are transparent.

4. The sensor as in claim 3 wherein said electroconductive members are a metallic film.

5. The sensor as in claim 1 wherein said substrate is a first substrate and further including additional substrates secured to an opposing major surface of said first substrate to form a composite assembly.

6. The sensor as in claim 1 wherein said first predetermined distance between said first and second electroconductive members is between approximately 1/16 to 5/32 inches and said second predetermined distance between said first and second electroconductive leads is between approximately $\frac{1}{8}$ to $\frac{3}{4}$ inches.

7. The sensor as in claim 5 wherein said first electroconductive members includes a first set of projections and said second electroconductive member includes a second set of projections, said first projections being positioned between and spaced from said second projections.

8. The sensor as in claim 7 wherein said leads extend along said first major surface of said first substrate to a peripheral edge of said assembly.

9. The sensor as in claim 1, wherein said predetermined characteristic is the voltage and/or current in said sensor and wherein said first predetermined distance is sufficiently different from said second predetermined distance so that said monitored voltage and/or current when only said electroconductive leads are electrically interconnected by moisture therebetween is measurably different from said monitored voltage and/or current when said electroconductive members said electroconductive members and leads are interconnected by moisture therebetween.

10. A sensor for detecting moisture comprising:
a dielectric substrate:
first and second electroconductive members positioned adjacent to each other and secured along a first major surface of said substrate and spaced apart a first predetermined distance, wherein adjacent portions of said first and second members have exposed, uncoated electroconductive surfaces;
first and second electroconductive leads extending from said first and second electroconductive members, respectively, and secured along said substrate surface wherein said leads are spaced apart a second predetermined distance and portions of said leads have exposed, uncoated electroconductive surfaces;
a signal generator electrically interconnected to said leads; and
means to monitor a predetermined characteristic of said sensor, wherein said first predetermined distance is sufficiently different from said second predetermined distance so that said monitored characteristic of said sensor when said leads are electrically interconnected by mositure therebetween is measurably different from said monitored characteristic when said electroconductive members or said electroconductive members and leads are electrically interconnected by moisture therebetween.

11. The sensor as in claim 10 wherein said monitoring means detects variations in the voltage and/or current in said sensor and wherein said first predetermined distance is sufficiently different from said second predetermined distance so that said monitored voltage and/or current when only said electroconductive leads are electrically interconnected by moisture therebetween is measurably different from said monitored voltage and/or current when said electroconductive members or said electroconductive members and leads are electrically interconnected by moisture therebetween.

12. The sensor as in claim 10 wherein said substrate and said electroconductive members are transparent.

13. The sensor as in claim 12 wherein said electroconductive members are a metallic film.

14. The sensor as in claim 10 wherein said substrate is a first substrate and further including additional substrates secured to an opposing major surface of said first substrate to form a composite assembly.

15. The sensor as in claim 14 wherein said predetermined characteristic is the impedance of said sensor and wherein said first predetermined distance is sufficiently different from said second predetermined distance so that said monitored sensor impedance when only said electroconductive leads are electrically interconnected by moisture therebetween is measurably different from said monitored sensor impedance when said electroconductive members or said electroconductive members and leads are electrically interconnected by moisture therebetween.

16. The sensor as in claim 14 wherein said monitoring means detects variations in the voltage and/or current in said sensor and wherein said first predetermined distance is sufficiently different from said second predetermined distance so that said monitored voltage and/or current when only said electroconductive leads are electrically interconnected by moisture therebetween is measurably different from said monitored voltage and/or current when said electroconductive members or said electroconductive members and leads are electrically interconnected by moisture therebetween.

17. The sensor as in claim 14 wherein said first electroconductive members includes a first set of projections and said second electroconductive member includes a second set of projections, said first projections being positioned between and spaced from said second projections.

18. The sensor as in claim 17 wherein said leads extend along said first major surface of said first substrate to a peripheral edge of said assembly.

19. The sensor as in claim 14 wherein said composite assembly is a windshield and further including means responsive to said monitoring means to activate means to clear said first major surface of said first substrate.

20. The sensor as in claim 10 wherein said first predetermined distance between said first and second electroconductive members is between approximately 1/16 to 5/32 inches and said second predetermined distance between said first and second electroconductive leads is between approximately ⅝ to ¾ inches.

21. The sensor as in claim 10 wherein said monitoring means monitors the impedance of said sensor and wherein said first predetermined distance is sufficiently different from said second predetermined distance so that said monitored sensor impedance when only said electroconductive leads are electrically interconnected by moisture therebetween is measurably different from said monitored sensor impedance when said electroconductive members or said electroconductive members and leads are electrically interconnected by moisture therebetween.

22. A sensor for detecting moisture comprising:
a dielectric substrate:
first and second electroconductive members positioned adjacent to each other and secured along a first major surface of said substrate and spaced apart a first predetermined distance, wherein adjacent portions of said first and second members have exposed, uncoated electroconductive surfaces; and
first and second electroconductive leads extending from said first and second electroconductive members, respectively, and secured along said substrate surface wherein said leads are spaced apart a second predetermined distance and portions of said leads have exposed, uncoated electroconductive surfaces, wherein said first predetermined distance is sufficiently different from said second predetermined distance so that a predetermined electrical characteristic of said sensor indicates the presence or absence of moisture on selected portions of said sensor.

23. A method of detecting moisture on a dielectric substrate comprising:
positioning and securing first and second electroconductive members adjacent to each other along a first major surface of said substrate and spaced apart a first predetermined distance, wherein adjacent portions of said first and second members have exposed, uncoated electroconductive surfaces;
extending and securing first and second electroconductive leads from said first and second electroconductive members, respectively, along said substrate surface, wherein said leads are spaced apart a second predetermined distance and portions of said leads have exposed, uncoated electroconductive surfaces;
passing an electrical signal through said sensor; and monitoring variations in a predetermined characteristic of said sensor, wherein said first predetermined distance is sufficiently different from said second predetermined distance so that said monitored characteristic of said sensor when said leads are electrically connected by moisture therebetween is measurably different from said monitored characteristic when said members are interconnected by moisture therebetween.

24. The method as in claim 23 wherein said electrical signal has a voltage and current and said monitoring step includes monitoring variations in said voltage and/or current of said electrical signal.

25. The method as in claim 23 further including the step of clearing said major surface of said substrate and said first and second electroconductive members in response to a monitored characteristic indicative of moisture electrically interconnecting said members.

26. The method as in claim 23 wherein said positioning step includes spacing said first and second electroconductive members apart a distance between approximately 1/16 to 5/32 inches and said extending step includes spacing said leads apart a distance between approximately ⅝ to 102 inches.

27. A sensor for detecting moisture comprising:
a dielectric substrate;
first and second electroconductive members secured to a first major surface of said substrate and positioned adjacent to each other and spaced apart a predetermined distance, wherein adjacent portions of said first and second members have exposed, uncoated electroconductive surfaces;
first and second electroconductive leads secured to said first major surface of said substrate and extending from said first and second electroconductive members, respectively, wherein said leads are spaced apart a second predetermined distance different from said first predetermined distance, and portions of said leads have exposed uncoated electroconductive surfaces, said sensor having a first electrical characteristic when moisture interconnects only said first and second leads, indicating a first operating condition, and a second electrical characteristic, different from said first electrical characteristic when moisture at least interconnects said first and second electroconductive members, indicating a second operating condition; and
means to permit electrical connection of said leads to controller having a signal generator and a signal monitoring means capable of detecting a change in the electrical characteristic of said sensor from said first electrical characteristic to said second electrical characteristic.

28. A sensor for detecting moisture comprising:
a dielectric substrate;
first and second electroconductive members secured to a first major surface of said substrate and positioned adjacent to each other and spaced apart a predetermined distance wherein adjacent portions of said first and second members have exposed uncoated electroconductive surfaces;
first and second electroconductive leads secured to said first major surface of said substrate and extending from said first and second electroconductive members, respectively, wherein said leads are spaced apart a second predetermined distance different from said first predetermined distance and portions of said leads have exposed uncoated electroconductive surfaces, said sensor having a first electrical characteristic when moisture interconnects only said first and second leads, indicating a first operating condition, and a second electrical characteristic, different from said first electrical characteristic, when moisture at least interconnects said first and second electroconductive members, indicating a second operating condition; and
a controller electrically connected to said leads and having a signal generating means and a signal monitoring means, wherein said monitoring means of capable of detecting a change in the electrical characteristic of said sensor from said first electrical characteristic to said second electrical characteristic.

29. A method of detecting moisture on a dielectric substrate comprising:

securing first and second electroconductive members to a first major surface of said substrate, said members being adjacent to each and spaced apart a first predetermined distance wherein adjacent portions of said first and second members having exposed uncoated electroconductive surfaces;

securing first and second electroconductive leads extending from said first and second electroconductive members, respectively, to said substrate surface wherein said leads are spaced apart a second predetermined distance different from said first predetermined distance and portions of said leads have exposed, uncoated electroconductive surfaces, and further wherein said sensor has a first electrical characteristic when moisture interconnects only said first and second electroconductive leads, indicating a first operating condition, and a second electrical characteristic, different from said first electrical characteristic, when moisture at least interconnects said first and second electroconductive members, indicating a second operating condition;

passing an electrical signal through said sensor;

monitoring said electrical characteristic of said sensor; and activating means to remove moisture from said sensor when said monitoring step detects said second electrical characteristic and deactivating said removal means when said monitoring step detects said first electrical characteristic.

* * * * *

UNITED STATES PATENT AND TRADEMARK OFFICE
CERTIFICATE OF CORRECTION

PATENT NO. : 5,040,411
DATED : August 20, 1991
INVENTOR(S) : Joseph Medzius It is certified that error appears in the above-identified patent and that said Letters Patent is hereby corrected as shown below:

Column 9, line 35, "1/8" should be --5/8--.

Column 9, line 53, after the word "members" there should be the word --or--.

Signed and Sealed this

Seventh Day of December, 1993

Attest:

BRUCE LEHMAN

*Attesting Officer*     Commissioner of Patents and Trademarks